(12) United States Patent
Tan et al.

(10) Patent No.: US 10,407,389 B2
(45) Date of Patent: Sep. 10, 2019

(54) METHOD FOR THE PREPARATION OF H-ARG(MIS)-OH

(71) Applicant: POLYPEPTIDE LABORATORIES HOLDING (PPL) AB, Limhamn (SE)

(72) Inventors: Deyong Tan, Guangzhou (CN); Joanna Dai, Chongqing (CN); Matthieu Giraud, Sion (CH); Fernando Albericio Palomera, Barcelona (ES)

(73) Assignee: POLYPEPTIDE LABORATORIES HOLDING (PPL) AB, Limhamn (SE)

( * ) Notice: Subject to any disclaimer, the term of this patent is extended or adjusted under 35 U.S.C. 154(b) by 0 days.

(21) Appl. No.: 15/569,221

(22) PCT Filed: Oct. 9, 2016

(86) PCT No.: PCT/CN2016/101558
§ 371 (c)(1),
(2) Date: Oct. 25, 2017

(87) PCT Pub. No.: WO2018/064829
PCT Pub. Date: Apr. 12, 2018

(65) Prior Publication Data
US 2019/0241517 A1    Aug. 8, 2019

(51) Int. Cl.
*C07D 209/30*    (2006.01)

(52) U.S. Cl.
CPC .................... *C07D 209/30* (2013.01)

(58) Field of Classification Search
None
See application file for complete search history.

(56) References Cited

U.S. PATENT DOCUMENTS 8,431,720 B2 *    4/2013    Giraud ............... C07D 209/30
548/484

FOREIGN PATENT DOCUMENTS

WO    WO 2009/135645    11/2009

OTHER PUBLICATIONS

International Search Report and Opinion for PCT/CN2016/101558, dated Jul. 4, 2017, 9 pages.
Isidro, Albert et al., 1, 2-Dimethylindole-3-sulfonyl (MIS) as protecting group for the side chain of arginine, Organic & Biomolecular Chemistry, Apr. 23, 2009, No. 12 vol. 7, pp. 2565-2569.

* cited by examiner

*Primary Examiner* — Kamal A Saeed
(74) *Attorney, Agent, or Firm* — Dority & Manning, P.A.

(57) ABSTRACT

The invention discloses a method for the preparation of N-omega-(1,2-dimethylindole-3-sulfonyl)-L-arginine and its derivatives using L-ornithine.

8 Claims, No Drawings

METHOD FOR THE PREPARATION OF H-ARG(MIS)-OH

CROSS REFERENCE TO RELATED APPLICATIONS

This application is the national stage entry of International Patent Application No. PCT/CN2016/101558 having a filing date of Oct. 9, 2016 and claims the benefit of U.S. Provisional Application No. 62/413,765 filed with the United States Patent and Trademark Office on Oct. 27, 2016, and claims priority to and the benefit of European Patent Application No. 16196502.5 filed in the European Patent Office on Oct. 31, 2016, the entire contents of which are incorporated herein by reference.

FIELD OF THE INVENTION

The invention discloses a method for the preparation of N-omega-(1,2-dimethylindole-3-sulfonyl)-L-arginine and its derivatives using L-ornithine.

BACKGROUND OF THE INVENTION

WO 2009/135645 A1 ("WO'645") discloses a new protecting group for Arg that is derived from indole-3-sulfonyl chloride. It can advantageously be used in peptide synthesis for protecting Arg or other amino acids and has better performance compared to hitherto known protecting groups such as Pbf, this better performance is exemplified in WO'645.

The method for preparation for Arg protected with MIS in the form of H-Arg(MIS)-OH, that is disclosed in WO'645 in examples 1 to 4, has the sequence as given in Formula Scheme 1:

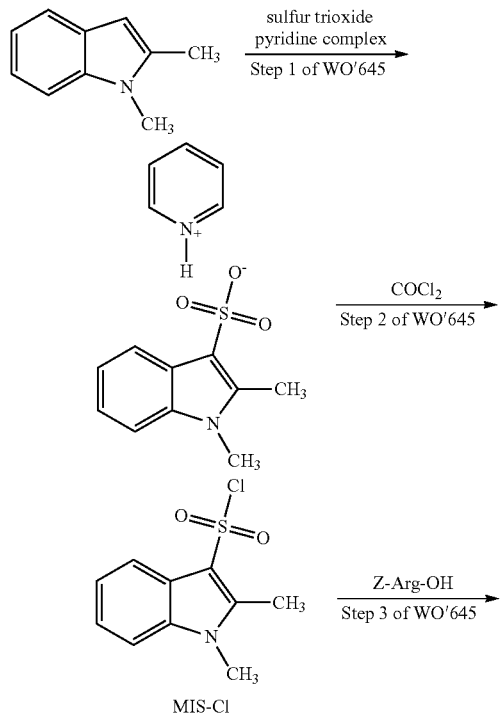

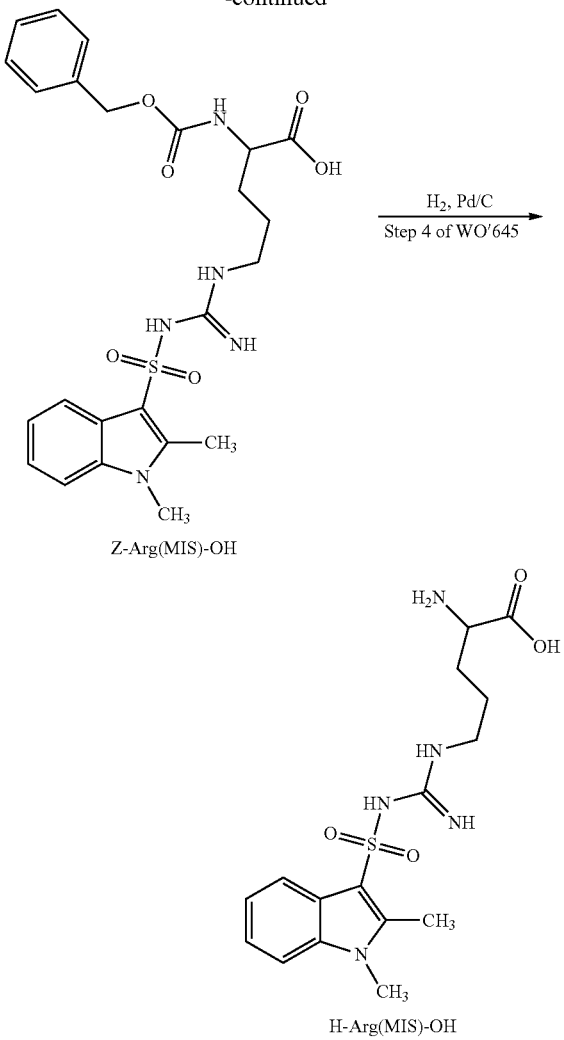

The yield of the steps is given in WO'645 with 96% for Step 1, 78% for Step 2, 18% for Step 3 and 98% for Step 4. Especially Step 3 of WO'645 shows a low yield.

There was a need for a method for preparation of H-Arg(MIS)-OH with a better yield than disclosed in WO'645.

The method of present invention shows higher yield.

The following abbreviations and meanings are used, if not stated otherwise:

Compound of formula (1) 1,2-dimethyl-1H-indol, 1,2-dimethylindol
Compound of formula (2) MIS-OH.Py, Pyridinium 1,2-dimethyl-1H-indole-3-sulfonate
Compound of formula (3) MIS-Cl, 1,2-Dimethyl-1H-indole-3-sulfonyl chloride
Compound of formula (5) L-Arg(MIS)-OH
Compound of formula (6) Fmoc-Arg(MIS)-OH
Compound of formula (PYCAAM) Pyrazole-1-carboxamidine
Compound of formula (SULPYR) sulphur trioxide pyridine complex
DMF Dimethylformamide
DIPEA Diisopropylethylamin
DMAA Dimethylacetamide
DMPU 1,3-Dimethyl-3,4,5,6-tetrahydro-2(1H)-pyrimidinone DMSO Dimethyl sulfoxide
EDTA Ethylenediaminetetraacetic acid
Fmoc fluoren-9-ylmethoxycarbonyl
Fmoc-OSu Fmoc N-hydroxysuccinimide ester, compound of formula (Fmoc-OSu)
halogen F, Cl, Br or I, preferably F, Cl or Br, more preferably F or Cl; even more preferably Cl
L-Orn.HCl L-ornithine hydro chloride
MTBE Methyl tert-butyl ether
MIS 1,2-dimethylindol-3-sulfonyl
NMP N-Methyl-2-pyrrolidone
Pbf 2,2,4,6,7-pentamethyldihydrobenzofuran-5-sulfonyl
WO'645 WO 2009/135645 A1
Z benzyloxycarbonyl

SUMMARY OF THE INVENTION

Subject of the invention is a method for the preparation of a compound of formula (V)

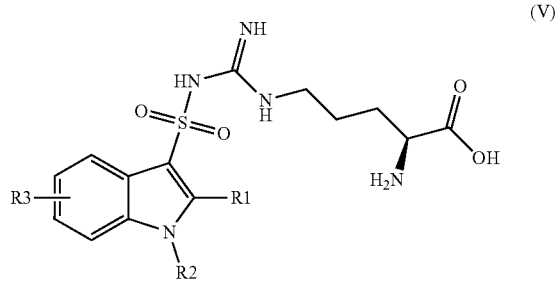

by a reaction REAC4, wherein a compound of formula (IV)

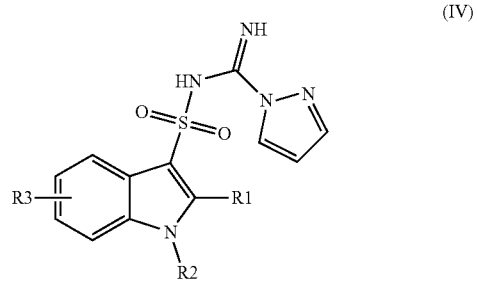

is reacted with L-ornithine;
R1 is H, $C_{1-6}$ alkyl, $C_{1-6}$ alkoxy or $C_{1-6}$ alkylthio;
R2 is $C_{1-6}$ alkyl, $C_{1-6}$ alkoxy or $C_{1-6}$ alkylthio;
or R1 and R2 together form a moiety of formula —(CH$_2$)n-, n 3, 4 or 5;
R3 is H, halogen, $C_{1-6}$ alkyl, $C_{1-6}$ alkoxy, $C_{1-6}$ alkylthio, phenyl or benzyl.

DETAILED DESCRIPTION OF THE INVENTION

Preferably,
R1 is $C_{1-4}$ alkyl, $C_{1-4}$ alkoxy or $C_{1-4}$ alkylthio;
R2 is $C_{1-4}$ alkyl, $C_{1-4}$ alkoxy or $C_{1-4}$ alkylthio;
R3 is H, halogen, $C_{1-4}$ alkyl, $C_{1-4}$ alkoxy, $C_{1-4}$ alkylthio, phenyl or benzyl;
more preferably,
R1 is $C_{1-4}$ alkyl, $C_{1-4}$ alkoxy or $C_{1-4}$ alkylthio;
R2 is $C_{1-4}$ alkyl, $C_{1-4}$ alkoxy or $C_{1-4}$ alkylthio;
R3 is H, halogen, $C_{1-4}$ alkyl, $C_{1-4}$ alkoxy or $C_{1-4}$ alkylthio;
even more preferably,
R1 is $C_{1-4}$ alkyl or $C_{1-4}$ alkoxy;
R2 is $C_{1-4}$ alkyl or $C_{1-4}$ alkoxy;
R3 is H, halogen, $C_{1-4}$ alkyl or $C_{1-4}$ alkoxy;
especially,
R1 is $C_{1-4}$ alkyl or $C_{1-4}$ alkoxy;
R2 is $C_{1-4}$ alkyl or $C_{1-4}$ alkoxy;
R3 is H or halogen;
more especially,
R1 is $C_{1-2}$ alkyl or $C_{1-2}$ alkoxy;
R2 is $C_{1-2}$ alkyl or $C_{1-2}$ alkoxy;
R3 is H or halogen;
even more especially,
R1 is $C_{1-2}$ alkyl;
R2 is $C_{1-2}$ alkyl;
R3 is H or halogen.
Preferably, REAC4 is done at a pH of from 9 to 12, more preferably of from 10 to 12, more preferably from 10.5 to 11.5.
Preferably, the pH is adjusted by the use of LiOH, NaOH or KOH, more preferably LiOH.
Preferably, L-ornithine is used in the form of its hydrochloride.
Preferably, the molar amount of L-ornithine is from 1 to 5 times, more preferably from 1 to 3 times, even more preferably from 1 to 2.5 times, of the molar amount of the compound of formula (IV).
Preferably, the reaction temperature TEMP4 of REAC4 is from 0 to 100° C., more preferably from 10 to 80° C.
Preferably, the pressure PRESS4 of REAC4 is adjusted according to the vapor pressure of the reaction mixture at the chosen TEMP4 of REAC4; but PRESS4 can also be adjusted to a higher pressure than the vapor pressure of the reaction mixture at the chosen TEMP4. A PRESS4 higher than the vapor pressure of the reaction mixture at the chosen TEMP4 can be adjusted for example by applying inert gas such a nitrogen or argon to the reaction vessel;
more preferably, REAC4 is done at a pressure from atmospheric pressure to 20 bar, more preferably from atmospheric pressure to 10 bar, even more preferably from atmospheric pressure to 5 bar, REAC4 is done at atmospheric pressure.
Preferably, the reaction time TIME4 of REAC4 is from 6 h to 48 h, more preferably from 12 h to 36 h, and even more preferably from 12 h to 24 h.
REAC4 can be performed under an atmosphere of air or under an atmosphere of an inert gas, such as nitrogen or such as a noble gas, such as argon.
REAC4 can be done in a solvent SOLV4, SOLV4 is preferably water, acetonitrile, MeOH, DMF, DMSO, tetramethylurea, DMPU, or a mixture thereof;
more preferably water, acetonitrile, or a mixture thereof.
Preferably, REAC4 is done in SOLV4.
After REAC4, the compound of formula (V) can be isolated and purified by conventional methods, which are known to those skilled in the art. These conventional methods include extraction, chromatography, or any combination of these methods of purification.
Preferably, after REAC4, the compound of formula (V) is precipitated by the addition of a salt of Cu(II), preferably the salt of Cu(II) is CuCl$_2$, CuSO$_4$, or Cu(NO$_3$)$_2$; more preferably CuCl$_2$.

In case of said precipitation a salt of Cu(II), the Cu(II) is preferably removed by known methods such as filtration, washing of the filter cake with water or EtOH, or extraction with a substance that forms an salt with Cu(II), such as EDTA, or a combination of these methods. More preferably, after REAC4, the compound of formula (V) is isolated by precipitation by the addition of a salt of Cu(II), filtration of the precipitate, washing of the filter cake formed by the filtration, preferably with water and EtOH, mixing the filter cake with water and using EDTA for removal of residual Cu(II) ions.

Preferably, the molar amount of the Cu(II) salt is from 0.1 to 10 times, more preferably of from 0.5 to 5 times, of the molar amount of the compound of formula (IV).

Preferably, the compound of formula (IV) is prepared by a reaction REAC3 of a compound of formula (III) with a compound of formula (PYCAAM);

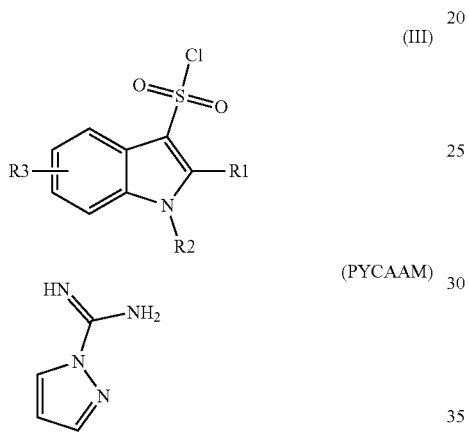

with R1, R2 and R3 as defined herein, also with all their embodiments.

Preferably, the compound of formula (PYCAAM) is used in REAC3 in the form of its hydrochloride.

Preferably, the molar amount of the compound of formula (PYCAAM) is from 1 to 5 times, more preferably from 1 to 3 times, even more preferably from 1 to 2 times, of the molar amount of the compound of formula (III).

Preferably, the reaction temperature TEMP3 of REAC3 is from 0 to 100° C., more preferably from 0 to 80° C., even more preferably from 10 to 60° C., especially from 10 to 40° C., more especially from 15 to 30° C.

Preferably, the pressure PRESS3 of REAC3 is adjusted according to the vapor pressure of the reaction mixture at the chosen TEMP3 of REAC4; but PRESS3 can also be adjusted to a higher pressure than the vapor pressure of the reaction mixture at the chosen TEMP3. A PRESS3 higher than the vapor pressure of the reaction mixture at the chosen TEMP3 can be adjusted for example by applying inert gas such a nitrogen or argon to the reaction vessel;

more preferably, REAC3 is done at a pressure from atmospheric pressure to 20 bar, more preferably from atmospheric pressure to 10 bar, even more preferably from atmospheric pressure to 5 bar, REAC3 is done at atmospheric pressure.

Preferably, the reaction time TIME3 of REAC3 is from 6 h to 48 h, more preferably from 12 h to 36 h, and even more preferably from 12 h to 24 h.

REAC3 can be performed under an atmosphere of air or under an atmosphere of an inert gas, such as nitrogen or such as a noble gas, such as argon.

REAC3 can be done in a solvent SOLV3, SOLV3 is preferably $C_{1-4}$ alkyl nitrile, dichlorethane, methylene chloride, triethyl amine, diisopropyl amine, MTBE, DMSO, DMF, DMAA, NMP, or a mixture thereof; more preferably acetonitrile.

Preferably, REAC3 is done in SOLV3.

After REAC3, the compound of formula (IV) can be isolated and purified by conventional methods, which are known to those skilled in the art. These conventional methods include extraction, crystallization, chromatography, or any combination of these methods of purification.

Preferably, the compound of formula (III) is prepared by a reaction REAC2 of a compound of formula (II) with a halogenating agent HALAG2;

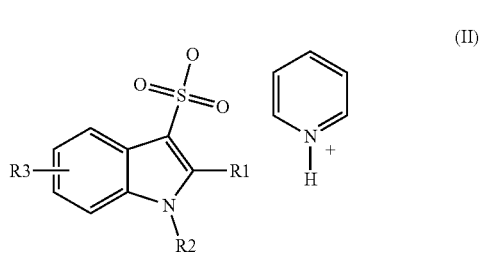

with R1, R2 and R3 as defined herein, also with all their embodiments.

Preferably, HALAG2 is selected from the group consisting of oxalyl chloride, thionylchloride, phosgene, diphosgene, triphosgene, $POCl_3$, $PCl_5$, $Cl_2$ in the presence of triphenylphoshine, cyanuric chloride, and methansulfonic acid chloride;

more preferably, HALAG2 is oxalyl chloride.

Preferably, the molar amount of HALAG2 is from 1 to 5 times, more preferably from 1 to 3 times, even more preferably from 1 to 2 times, of the molar amount of the compound of formula (II).

REAC2 can be done in the presence of a base BAS2; preferably, BAS2 is DMF, picoline, quinoline, pyrimidine, N—$C_{1-2}$ alkyl imidazole;

more preferably, BAS2 is DMF.

Preferably, the molar amount of BAS2 is from 0.01 to 1 times, more preferably from 0.05 to 0.5 times, even more preferably from 0.05 to 0.3 times, of the molar amount of the compound of formula (II).

Preferably, the reaction temperature TEMP2 of REAC2 is from −10 to 50° C., more preferably from −10 to 20° C., even more preferably from −10 to 10° C.

Preferably, the pressure PRESS2 of REAC2 is adjusted according to the vapor pressure of the reaction mixture at the chosen TEMP2 of REAC2; but PRESS2 can also be adjusted to a higher pressure than the vapor pressure of the reaction mixture at the chosen TEMP2. A PRESS2 higher than the vapor pressure of the reaction mixture at the chosen TEMP2 can be adjusted for example by applying inert gas such a nitrogen or argon to the reaction vessel;

more preferably, REAC2 is done at a pressure from atmospheric pressure to 20 bar, more preferably from atmospheric pressure to 10 bar, even more preferably from atmospheric pressure to 5 bar, especially, REAC2 is done at atmospheric pressure.

Preferably, the reaction time TIME2 of REAC2 is from 1 h to 12 h, more preferably from 1 h to 6 h.

REAC2 can be performed under an atmosphere of air or under an atmosphere of an inert gas, such as nitrogen or such as a noble gas, such as argon.

REAC2 can be done in a solvent SOLV2, SOLV2 is preferably dichloromethane, dichloroethylene, chlorobenzene, toluene, MTBE, $C_{2-4}$ alkyl acetate, triethylamine, diisopropyl amine;
more preferably dichloromethane.

Preferably, REAC2 is done in SOLV2.

Preferably, after REAC2 a quencher such as water is added to the reaction mixture.

Preferably, the amount of water, that is added, is from 0.1 to 20 times, more preferably from 0.1 to 10 times, of the weight of the reaction mixture.

After REAC2, the compound of formula (III) can be isolated and purified by conventional methods, which are known to those skilled in the art. These conventional methods include extraction, crystallization, chromatography, or any combination of these methods of purification.

Preferably, the compound of formula (II) is prepared by a reaction REAC1 of a compound of formula (I)

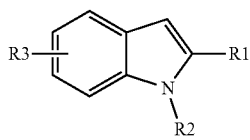
(I)

with a compound SULFON;

SULFON is selected from the group consisting of a compound of formula (SULPYR), chloro sulfonic acid and oleum;

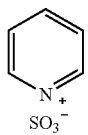
(SULPYR)

with R1, R2 and R3 as defined herein, also with all their embodiments.

Preferably SULFON is a compound of formula (SULPYR).

Preferably, the molar amount of SULFON is from 1 to 5 times, more preferably from 1 to 3 times, even more preferably from 1 to 2 times, of the molar amount of the compound of formula (I).

Preferably, the reaction temperature TEMP1 of REAC1 is from 0 to 100° C., more preferably from 10 to 80° C., even more preferably from 20 to 80° C., especially from 30 to 60° C.

Preferably, the pressure PRESS1 of REAC1 is adjusted according to the vapor pressure of the reaction mixture at the chosen TEMP1 of REAC1; but PRESS1 can also be adjusted to a higher pressure than the vapor pressure of the reaction mixture at the chosen TEMP1. A PRESS1 higher than the vapor pressure of the reaction mixture at the chosen TEMP1 can be adjusted for example by applying inert gas such a nitrogen or argon to the reaction vessel;

more preferably, REAC1 is done at a pressure from atmospheric pressure to 20 bar, more preferably from atmospheric pressure to 10 bar, even more preferably from atmospheric pressure to 5 bar, especially, REAC1 is done at atmospheric pressure.

Preferably, the reaction time TIME1 of REAC1 is from 1 h to 12 h, more preferably from 1 h to 8 h.

REAC1 can be performed under an atmosphere of air or under an atmosphere of an inert gas, such as nitrogen or such as a noble gas, such as argon.

REAC1 can be done in a solvent SOLV1, SOLV1 is preferably dichloromethane, chlorobenzene, dichlorethane, pyridine, picoline, quinoline or a mixture thereof; preferably dichloromethane.

Preferably, REAC1 is done in SOLV1.

Preferably, SOLV1 and SOLV2 are identical.

After REAC1, the compound of formula (II) can be isolated and purified by conventional methods, which are known to those skilled in the art. These conventional methods include extraction, crystallization, chromatography, or any combination of these methods of purification.

Preferably, the compound of formula (II) is not isolated.

Preferably, the compound of formula (II) is used in REAC2 in the form of the reaction mixture obtained from REAC1.

The compound of formula (I) and SULFON are known compounds and can be prepared by known methods.

Another of the invention is the use of a compound of formula (V) for the preparation of a compound of formula (VI);

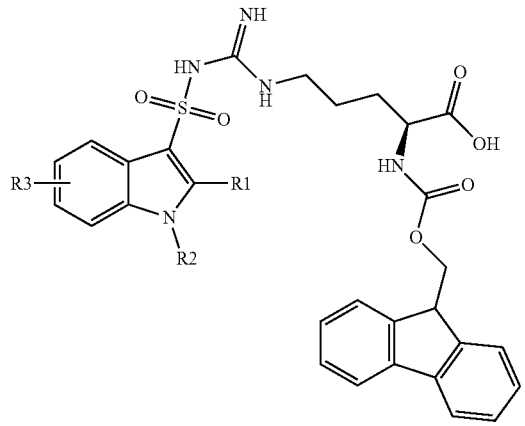
(VI)

with R1, R2 and R3 as defined herein, also with all their embodiments.

Another of the invention is the method for the preparation of a compound of formula (VI) by a reaction REAC5 of a compound of formula (V) with a compound FMOCACT;

FMOCACT is an activated form of Fmoc, preferably such as Fmoc-Cl or a compound of formula (Fmoc-OSu).

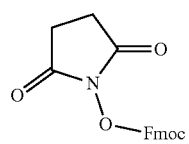
(Fmoc-OSu)

Preferably, the compound of formula (V) has been prepared by REAC4, with REAC4 as described herein.

Preferably FMOCACT is a compound of formula (Fmoc-OSu).

Preferably, the molar amount of FMOCACT is from 1 to 5 times, more preferably from 1 to 3 times, even more preferably from 1 to 2 times, of the molar amount of the compound of formula (V).

Preferably, the reaction temperature TEMP5 of REAC5 is from 0 to 100° C., more preferably from 10 to 80° C., even more preferably from 10 to 60° C., especially from 10 to 40° C.

Preferably, the pressure PRESS5 of REAC5 is adjusted according to the vapor pressure of the reaction mixture at the chosen TEMP5 of REAC5; but PRESS5 can also be adjusted to a higher pressure than the vapor pressure of the reaction mixture at the chosen TEMP5. A PRESS5 higher than the vapor pressure of the reaction mixture at the chosen TEMP5 can be adjusted for example by applying inert gas such a nitrogen or argon to the reaction vessel;

more preferably, REAC5 is done at a pressure from atmospheric pressure to 20 bar, more preferably from atmospheric pressure to 10 bar, even more preferably from atmospheric pressure to 5 bar, especially, REAC5 is done at atmospheric pressure.

Preferably, the reaction time TIME5 of REAC5 is from 1 h to 12 h, more preferably from 1 h to 8 h, even more preferably from 1 h to 6 h.

REAC5 can be performed under an atmosphere of air or under an atmosphere of an inert gas, such as nitrogen or such as a noble gas, such as argon.

REAC5 can be done in a solvent SOLV5, SOLV5 is preferably water, acetonitrile, dichlorethane, methylenchloride, toluene, MTBE, DMAA, tetramethylurea, or a mixture thereof;

more preferably water, acetonitrile or a mixture thereof.

Preferably, REAC5 is done in SOLV5.

After REAC5, the compound of formula (VI) can be isolated and purified by conventional methods, which are known to those skilled in the art. These conventional methods include extraction, crystallization, chromatography, or any combination of these methods of purification.

A preferred embodiment of the compound of formula (V) is a compound of formula (5).

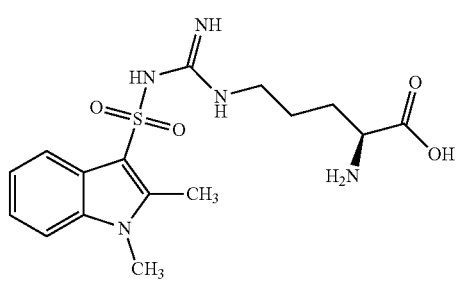

(5)

A preferred embodiment of the compound of formula (IV) is a compound of formula (4).

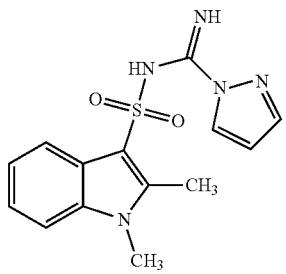

(4)

A preferred embodiment of the compound of formula (III) is a compound of formula (3).

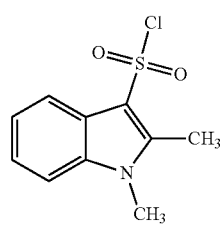

(3)

A preferred embodiment of the compound of formula (II) is a compound of formula (2).

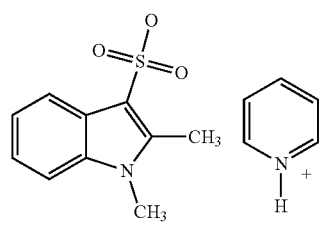

(2)

A preferred embodiment of the compound of formula (I) is a compound of formula (1).

A preferred embodiment of the compound of formula (VI) is a compound of formula (6).

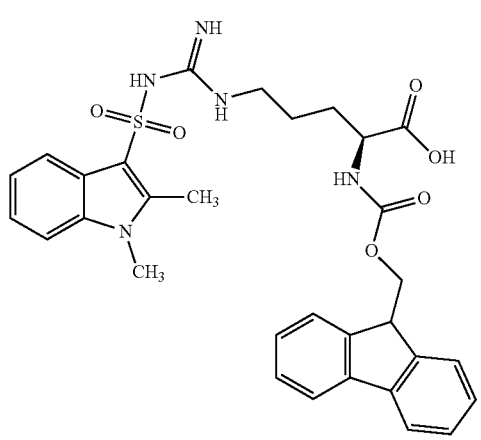

(6)

EXAMPLES

Methods:

HPLC for Examples 1, 2 and 3:

| | |
|---|---|
| Mobile phase A: | 0.045% TFA in water |
| Mobile phase B: | 0.036% TFA in Acetonitrile |
| Column | ZORBAX Eclipse ™ XDB-$C_8$ 5 micrometer; 4.6 × 150 mm; S.N. USRK041807 |
| Flow | 1 mL/min |
| Injection | 2 microL |
| UV | 254 nm |

| Gradient | Time [min] | A [%] | B [%] |
|---|---|---|---|
| | 0 | 95 | 5 |
| | 15 | 0 | 100 |
| | 15.1 | 95 | 5 |
| | 20 | 95 | 5 |

HPLC for Examples 5 - purity:

| | |
|---|---|
| Mobile phase A: | 0.1% TFA in water |
| Mobile phase B: | 0.1% TFA in Acetonitrile |
| Column | Xterra RP C18; 5 micrometer; 4.6 × 150 mm |
| Flow | 1 mL/min |
| Injection | 2 microL |
| UV | 254 nm |

| Gradient | Time [min] | A [%] | B [%] |
|---|---|---|---|
| | 0 | 95 | 5 |
| | 20 | 5 | 95 |
| | 25 | 5 | 95 |
| | 25.1 | 95 | 5 |

HPLC for Example 5 - Chiral purity:

| | |
|---|---|
| Mobile phase A: | Ammonium acetate buffer 100 mM, pH = 6.0 (7.71 gr Ammonium Acetate are dissolved in 1000 ml water, the solution is adjusted to pH = 6.0 with glacial acetic acid) |
| Mobile phase B: | Methanol |
| Column | ChiralPak QN-AX; 150 × 4.6 mm; 5 micrometer |
| Flow | 1 mL/min |
| Injection | 10 microL |
| concentration | 1 mg/mL |
| UV | 254 nm |

| Isocratic | A [%] | B [%] |
|---|---|---|
| | 25 | 75 |

Example 1, Synthesis of MIS-OH.Py, Compound of Formula (2)

1,2-Dimethylindole (1.00 kg, 6.88 mol, 1.00 eq), sulphur trioxide pyridine complex (1.42 kg, 8.88 mol, 1.29 eq) and dichloromethane (6.7 kg) were mixed. The mixture was heated to 40° C. and kept for 4 h at 40° C. The conversion reached 99.5% as determined by HPLC. If the value is not reached, then 0.03 eq of sulphur trioxide pyridine complex can be added and stirring can be continued at 40° C. for 1 h. The reaction mixture was cooled down to 20 to 30° C. and was used for next step (based on the assumption of 100% yield, containing 2.09 kg of MIS-OH.Py, 6.88 mol).

The structure was confirmed by $^1$H NMR.

Example 2, Synthesis of MIS-Cl, Compound of Formula (3)

To the reaction mixture containing MIS-OH.Py in dichloromethane, prepared according to example 1, were added 12.7 kg of dichloromethane. DMF (50 g, 0.68 mol, 0.1 eq) was added. The reaction mixture was cooled down to 0 to 5° C. Oxalyl chloride (1.19 kg, 9.34 mol, 1.36 eq) was added dropwise in 2 h while keeping the reaction temperature at 0 to 5° C. Then the reaction mixture was kept at 0 to 5° C. for 1 h. The conversion reached 99.5% by HPLC analysis.

The reaction mixture was quenched by addition of water (2.2 kg) at −5 to 5° C. while stirring. Two phases separated, the water phase was discarded. The organic phase was washed with water (twice with 2.0 kg) at 0 to 5° C. Dichloromethane (2.7 kg) was charged and the resulting mixture solution was heated to 25 to 30° C. Anhydrous $MgSO_4$ (700 g) was charged and the reaction mixture was stirred for 0.5 h. $MgSO_4$ was removed by filtration and the $MgSO_4$ filter cake was washed with dichloromethane (650 g), the filtrates were combined.

The combined filtrates were concentrated to about 2.3 kg under 250 to 300 mbar pressure and at 15 to 20° C. MIS-Cl was obtained by filtration and the filter cake was washed with a mixture of dichloromethane and hexane (v/v=1/1, 3 L). The collected pink MIS-Cl was dried at 15 to 20° C. for 15 h. 1.4 kg of MIS-Cl (84% yield, this is the combined yield of example 1 and example 2) was obtained with 99% HPLC purity.

The yield of example 1 and example 2 each was ca. 92%.

The structure was confirmed by $^1$H NMR and $^{13}$C NMR.

Example 3, Synthesis of Compound of Formula (4)

Pyrazole-1-carboxamidine hydrochloride (0.85 kg, 5.80 mol, 1.0 eq), MeCN (5.10 kg) and DIPEA (1.92 kg, 14.8 mol, 2.6 eq) were mixed. The temperature of mixture is adjusted to 18 to 22° C. A solution of MeCN (1.50 kg) and MIS-Cl (prepared according to example 2, 1.41 kg, 5.80 mol, 1.0 eq) was added dropwise in 0.5 to 1 h. The mixture was stirred at 18 to 22° C. for 16 h. The mixture was filtered and the obtained filter cake was washed with $H_2O$ (5.8 kg), followed by washing with MeCN (0.5 kg). The filter cake was dried at 38° C. and 5 mbar for 16 h. Compound of formula (4) (1.2 kg) was obtained as white solid with 98% HPLC purity, 65% isolation yield.

The structure was confirmed by $^1$H NMR and $^{13}$C NMR.

Example 4, Synthesis of L-Arg(MIS)-OH, Compound of Formula (5)

$H_2O$ (1.23 kg) and L-Orn.HCl (1.04 kg, 6.17 mol, 1.8 eq) were mixed, a solution of $LiOH.H_2O$ (0.41 kg, 9.95 mol, 2.9 eq) in $H_2O$ (3.50 kg) was added dropwise in 0.5 h at below 30° C. The mixture was heated to 50° C. and the pH was adjusted to 10.8 with a 3M aqueous solution of LiOH (about 1 kg). MeCN (1.58 kg) was added. Compound of formula (4) (prepared according to example 4, 1.1 kg, 3.43 mol, 1.0 eq) was added, then MeCN (1.0 kg) was added. The reaction mixture was stirred for 16 h at 60° C. A solution of $CuCl2.H_2O$ (0.57 kg, 3.77 mol, 1.1 eq) in water (1.93 kg) was added in 3 h at 60° C. The mixture, that was a solution a solution before the addition of the $CuCl_2$, became a suspension during the addition of the $CuCl_2$. The suspension was stirred for 2 h. The solid was collected by filtration at 60° C. and was washed with $H_2O$ (3 times with 5 kg, 60° C.), followed by washing with EtOH (4 kg, 60° C.).

The wet solid was mixed with $EDTA-2Na.2H_2O$ (1.15 kg, 3.08 mol, 0.9 eq) and $H_2O$ (7.7 kg). The mixture was heated to 65° C. and stirred for 3 h. The mixture was cooled to 0° C. in 3 h. The mixture was filtered and the filter cake was washed with $H_2O$ (3 times with 3 kg of 0° C.). Drying was done at 42° C. under a pressure below 15 mbar for 16 h. 1.02 kg of L-Arg(MIS)-OH were obtained, yield was 78%.

The structure was confirmed by $^1$H NMR and $^{13}$C NMR.

Example 5, Synthesis of Fmoc-Arg(MIS)-OH, Compound of Formula (6)

L-Arg(MIS)-OH (prepared according to example 4, 1.0 kg, 2.60 mol, 1.0 eq) was mixed with a solution of Na$_2$CO$_3$ (0.29 kg, 2.74 mol, 1.05 eq) in H$_2$O (5.3 kg), MeCN (7.1 kg) were charged. The mixture was stirred at 20° C. for 30 min, L-Arg(MIS)-OH was dissolved completely. A solution of Fmoc-OSu (0.87 kg, 2.60 mol, 1.0 eq) in MeCN (0.8 kg) was added dropwise in 15 min. The reaction mixture was stirred for another 3, the content of L-Arg(MIS)-OH was lower than 0.2% as determined by HPLC.

H$_2$O (5.3 kg) was added to the reaction mixture, the resulting mixture was washed with diisopropylethyl ether (3 times with 10 L). Ethyl acetate (36 kg) was added, the mixture was cooled to 0 to 5° C., the pH was adjusted to 3.8 to 4.0 with a 30 wt-% citric aqueous solution (about 3.3 kg) at 0 to 5° C. Two phases had formed and were separated, the organic phase was washed with water (3 times with 8 kg), the organic phase was concentrated to a 4 L suspension under 50 to 300 mbar at a jacket temperature of the reaction vessel of below 30° C. MeOH (5.9 kg) was charged and the concentration was continued to 4 L under 50 to 300 mbar at a jacket temperature of below 30° C. The product was collected by filtration and was dried under vacuum to give 1.2 kg product, yield: 80.1%.

The structure was confirmed by $^1$H NMR and $^{13}$C NMR.
Purity was 99.5%.
Chiral purity was 99.8%.

The invention claimed is:

1. A method for the preparation of a compound of formula (V)

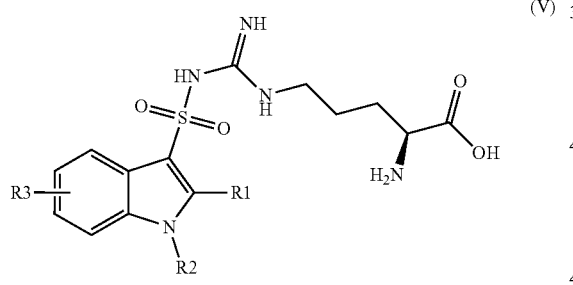

by a reaction REAC4, wherein a compound of formula (IV)

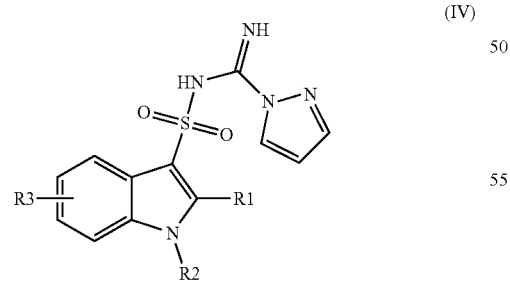

is reacted with L-ornithine;
R1 is H, C$_{1-6}$ alkyl, C$_{1-6}$ alkoxy or C$_{1-6}$ alkylthio;
R2 is C$_{1-6}$ alkyl, C$_{1-6}$ alkoxy or C$_{1-6}$ alkylthio;
or R1 and R2 together form a moiety of formula —(CH$_2$)n-,
n is 3, 4 or 5;
R3 is H, halogen, C$_{1-6}$ alkyl, C$_{1-6}$ alkoxy, C$_{1-6}$ alkylthio, phenyl or benzyl.

2. The method according to claim 1, wherein
R1 is C$_{1-4}$ alkyl, C$_{1-4}$ alkoxy or C$_{1-4}$ alkylthio;
R2 is C$_{1-4}$ alkyl, C$_{1-4}$ alkoxy or C$_{1-4}$ alkylthio;
R3 is H, halogen, C$_{1-4}$ alkyl, C$_{1-4}$ alkoxy, C$_{1-4}$ alkylthio, phenyl or benzyl.

3. The method according to claim 1, wherein
the compound of formula (IV) is prepared by a reaction REAC3 of a compound of formula (III) with a compound of formula (PYCAAM);

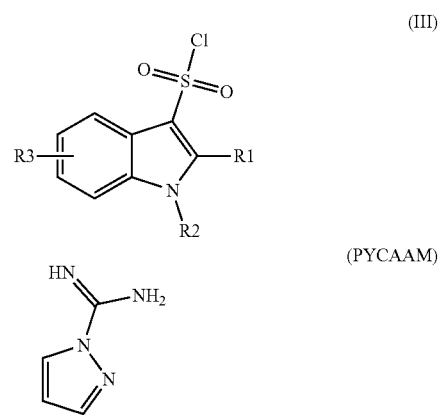

R1 is H, C$_{1-6}$ alkyl, C$_{1-6}$ alkoxy or C$_{1-6}$ alkylthio;
R2 is C$_{1-6}$ alkyl, C$_{1-6}$ alkoxy or C$_{1-6}$ alkylthio;
or R1 and R2 together form a moiety of formula —(CH$_2$)n-,
n is 3, 4 or 5;
R3 is H, halogen, C$_{1-6}$ alkyl, C$_{1-6}$ alkoxy, C$_{1-6}$ alkylthio, phenyl or benzyl.

4. The method according to claim 3, wherein
the compound of formula (III) is prepared by a reaction REAC2 of a compound of formula (II) with a halogenating agent HALAG2;

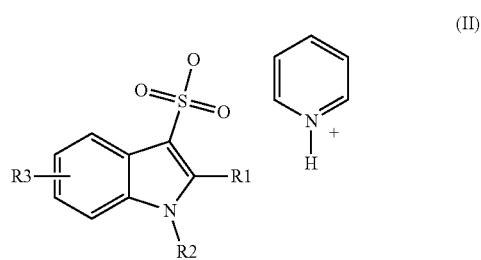

R1 is H, C$_{1-6}$ alkyl, C$_{1-6}$ alkoxy or C$_{1-6}$ alkylthio;
R2 is C$_{1-6}$ alkyl, C$_{1-6}$ alkoxy or C$_{1-6}$ alkylthio;
or R1 and R2 together form a moiety of formula —(CH$_2$)n-,
n is 3, 4 or 5;
R3 is H, halogen, C$_{1-6}$ alkyl, C$_{1-6}$ alkoxy, C$_{1-6}$ alkylthio, phenyl or benzyl.

5. The method according to claim 4, wherein
HALAG2 is selected from the group consisting of oxalyl chloride, thionylchloride, phosgene, diphosgene, triphosgene, POCl$_3$, PCl$_5$, Cl$_2$ in the presence of triphenylphoshine, cyanuric chloride, and methansulfonic acid chloride.

6. The method according to claim 4, wherein compound of formula (II) is prepared by a reaction REAC1 of compound of formula (I)

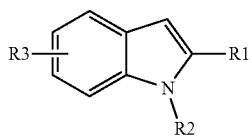
(I)

with compound SULFON, SULFON is selected from the group consisting of compound of formula (SULPYR), chloro sulfonic acid and oleum;

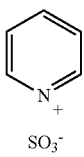
(SULPYR)

R1 is H, C$_{1-6}$ alkyl, C$_{1-6}$ alkoxy or C$_{1-6}$ alkylthio;
R2 is C$_{1-6}$ alkyl, C$_{1-6}$ alkoxy or C$_{1-6}$ alkylthio;
or R1 and R2 together form a moiety of formula —(CH$_2$)$_n$-,
n is 3, 4 or 5;
R3 is H, halogen, C$_{1-6}$ alkyl, C$_{1-6}$ alkoxy, C$_{1-6}$ alkylthio, phenyl or benzyl.

7. A method for the preparation of compound of formula (VI);

(VI)

R1 is H, C$_{1-6}$ alkyl, C$_{1-6}$ alkoxy or C$_{1-6}$ alkylthio;

R2 is C$_{1-6}$ alkyl, C$_{1-6}$ alkoxy or C$_{1-6}$ alkylthio;

or R1 and R2 together form a moiety of formula —(CH$_2$)$_n$-, n is 3, 4 or 5;

R3 is H, halogen, C$_{1-6}$ alkyl, C$_{1-6}$ alkoxy, C$_{1-6}$ alkylthio, phenyl or benzyl;

by a reaction REAC5 of compound of formula (V) with compound FMOCACT;

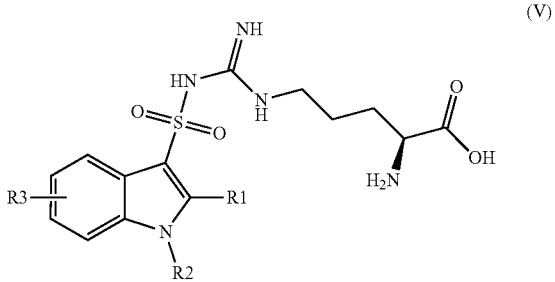
(V)

FMOCACT is an activated form of Fmoc;

and wherein compound of formula (V) has been prepared by REAC4, with REAC4 as defined in claim 1.

8. The method according to claim 7, wherein FMOCACT is Fmoc-Cl or compound of formula (Fmoc-OSu)

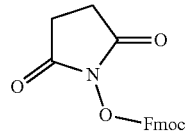
(Fmoc-OSu)

* * * * *